United States Patent
Lim et al.

(10) Patent No.: US 9,833,262 B2
(45) Date of Patent: Dec. 5, 2017

(54) SPINAL CORRECTION SYSTEM AND METHOD

(71) Applicant: Warsaw Orthopedic, Inc., Warsaw, IN (US)

(72) Inventors: Roy K. Lim, Germantown, TN (US); Matthew M. Morrison, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 471 days.

(21) Appl. No.: 14/450,831

(22) Filed: Aug. 4, 2014

(65) Prior Publication Data

US 2016/0030088 A1    Feb. 4, 2016

(51) Int. Cl.
*A61B 17/70* (2006.01)
*A61B 17/80* (2006.01)

(52) U.S. Cl.
CPC ...... *A61B 17/7014* (2013.01); *A61B 17/7005* (2013.01); *A61B 17/707* (2013.01); *A61B 17/7011* (2013.01); *A61B 17/8009* (2013.01); *A61B 17/8076* (2013.01)

(58) Field of Classification Search
CPC ............ A61B 17/7014; A61B 17/8009; A61B 17/8076; A61B 17/707; A61B 17/7005; A61B 17/7011
See application file for complete search history.

(56) References Cited

U.S. PATENT DOCUMENTS

| | | | | |
|---|---|---|---|---|
| 2,333,033 A * | 10/1943 | Mraz | ...................... | A61B 17/60 269/54.1 |
| 3,604,414 A * | 9/1971 | Borges | ............... | A61B 17/8019 606/105 |
| 4,157,715 A * | 6/1979 | Westerhoff | ......... | A61B 17/8004 606/58 |
| 5,129,903 A * | 7/1992 | Luhr | ................... | A61B 17/8004 606/282 |
| 5,700,263 A * | 12/1997 | Schendel | ............. | A61B 17/663 606/57 |
| 6,139,316 A * | 10/2000 | Sachdeva | ............. | A61B 17/663 433/7 |
| 7,029,472 B1 * | 4/2006 | Fortin | ................ | A61B 17/7047 606/105 |
| 7,942,908 B2 * | 5/2011 | Sacher | ............... | A61B 17/7014 606/258 |
| 7,951,152 B2 * | 5/2011 | Marino | .............. | A61B 17/7079 606/279 |
| 7,998,216 B2 * | 8/2011 | Elsalanty | ........... | A61B 17/8004 606/282 |
| 8,211,149 B2 * | 7/2012 | Justis | ................. | A61B 17/7017 606/105 |
| 2006/0004447 A1 * | 1/2006 | Mastrorio | .......... | A61B 17/7065 623/17.11 |
| 2006/0122606 A1 * | 6/2006 | Wolgen | ................ | A61B 17/663 606/71 |

(Continued)

*Primary Examiner* — Ellen C Hammond

(57) ABSTRACT

A spinal correction implant comprises a body extending between a first end and a second end. The body has a curvature. A first longitudinal element is connected with the first end. A ratchet is disposed with the body. A second longitudinal element is connected to the ratchet and is incrementally movable relative to the body. Systems and methods are disclosed.

20 Claims, 7 Drawing Sheets

(56) References Cited

U.S. PATENT DOCUMENTS

| | | | |
|---|---|---|---|
| 2006/0155279 A1* | 7/2006 | Ogilvie | A61B 17/6491 606/328 |
| 2006/0195087 A1* | 8/2006 | Sacher | A61B 17/7014 606/258 |
| 2008/0177319 A1* | 7/2008 | Schwab | A61B 17/7014 606/257 |
| 2009/0275988 A1* | 11/2009 | Baynham | A61B 17/7059 606/282 |
| 2009/0306717 A1* | 12/2009 | Kercher | A61B 17/7011 606/258 |
| 2010/0004697 A1* | 1/2010 | Fortin | A61B 17/66 606/86 R |
| 2012/0197403 A1* | 8/2012 | Merves | A61F 2/44 623/17.16 |
| 2013/0282064 A1* | 10/2013 | Arnin | A61B 17/7014 606/258 |
| 2013/0296857 A1* | 11/2013 | Barnett | A61B 17/6416 606/57 |
| 2013/0338713 A1* | 12/2013 | Kawakami | A61B 17/7014 606/258 |
| 2014/0276822 A1* | 9/2014 | Cresina | A61B 17/6416 606/57 |
| 2014/0296918 A1* | 10/2014 | Fening | A61B 17/7016 606/258 |
| 2016/0030088 A1* | 2/2016 | Lim | A61B 17/7014 606/257 |
| 2016/0199101 A1* | 7/2016 | Sharifi-Mehr | A61B 17/7017 606/258 |

* cited by examiner

SPINAL CORRECTION SYSTEM AND METHOD

TECHNICAL FIELD

The present disclosure generally relates to medical devices for the treatment of musculoskeletal disorders, and more particularly to a surgical system and method for correction of a spine disorder.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. Correction treatments used for positioning and alignment may employ implants, such as rods or tethers, for stabilization of a treated section of a spine. This disclosure describes an improvement over these prior art technologies.

SUMMARY

In one embodiment, a spinal correction implant is provided. The spinal correction implant comprises a body extending between a first end and a second end. The body has a curvature. A first longitudinal element is connected with the first end. A ratchet is disposed with the body. A second longitudinal element is connected to the ratchet and is incrementally movable relative to the body. In some embodiments, systems and methods are disclosed.

BRIEF DESCRIPTION OF THE DRAWINGS

The present disclosure will become more readily apparent from the specific description accompanied by the following drawings, in which.

DETAILED DESCRIPTION

Figure 1:
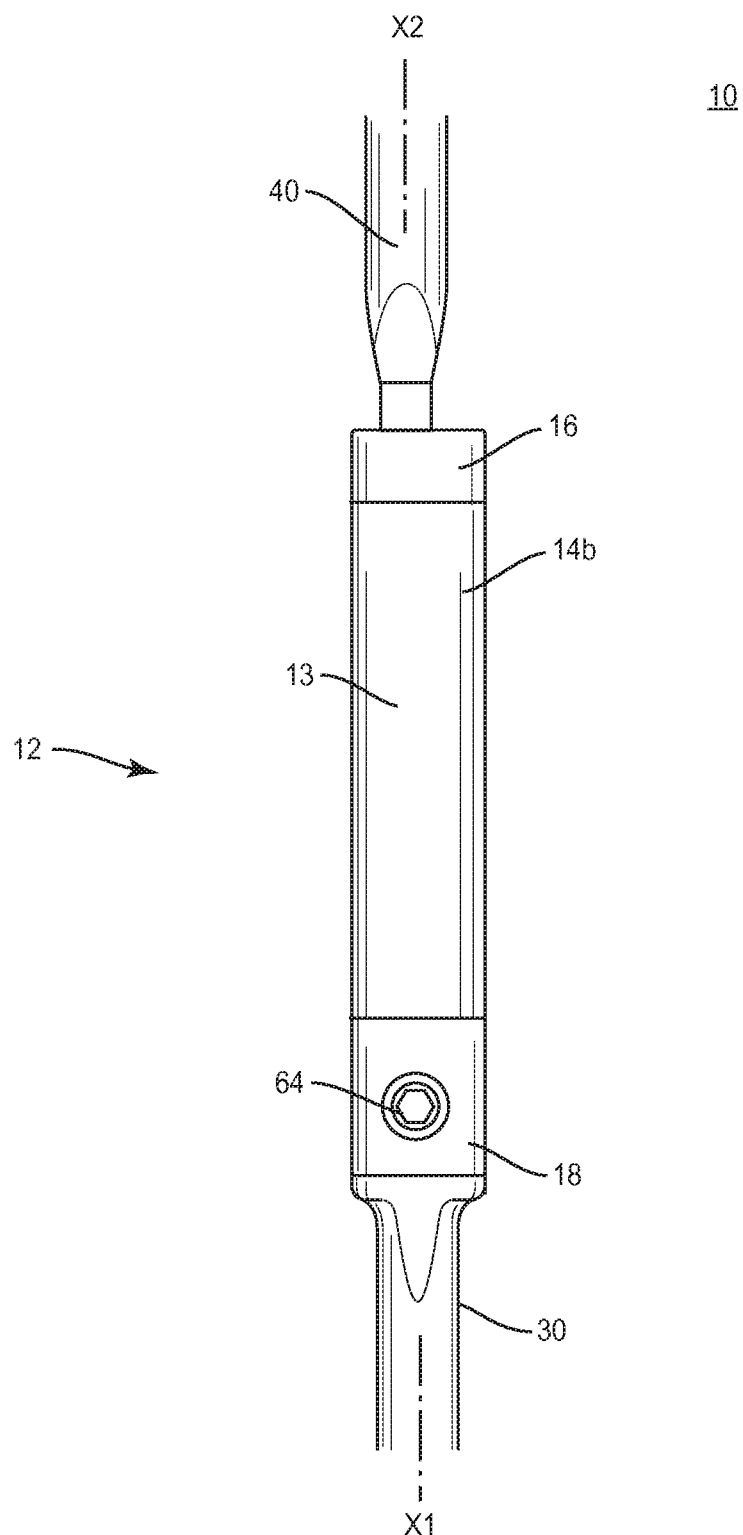
FIG. 1 is a side view of components of one embodiment of a spinal correction system in accordance with the principles of the present disclosure.
Figure 2:
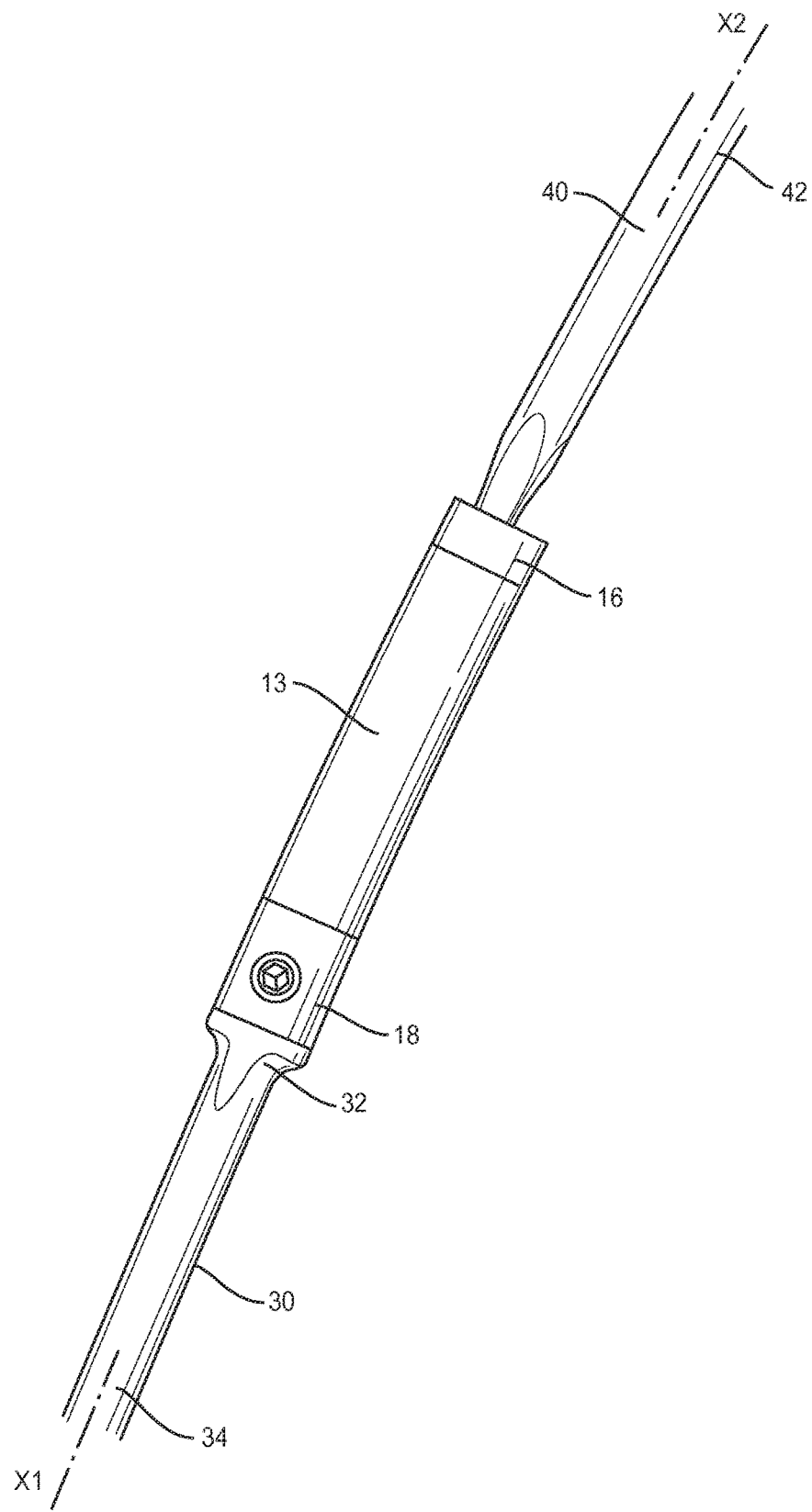
FIG. 2 is a perspective view of the components shown in FIG. 1.

The exemplary embodiments of the surgical system and related methods of use of the present disclosure are discussed in terms of medical devices for the treatment of musculoskeletal disorders and more particularly, in terms of a spinal correction system and a method. In some embodiments, the spinal correction system may be employed with a method for correction of deformities, such as, for example, kyphosis and scoliosis.

In one embodiment, a spinal correction system is employed with a method or procedure for treatment of patients having a scoliotic disorder and suffering from congenital chest wall deformation. In one embodiment, the spinal correction system includes a growing rod connected with a rib cage to expand and support a deformed chest wall. In some embodiments, this configuration provides treatment to aid lung function and development. In one embodiment, the spinal correction system includes a growing rod that is curved and disposable adjacent ribs. In some embodiments, this configuration provides treatment to directly distract the ribs.

In one embodiment, the spinal correction system comprises components that include a growth rod configured for use with children. In one embodiment, the growth rod includes a ratcheting mechanism with a back-up drive. In one embodiment, the growth rod includes a curved, flat and low profile. In one embodiment, the components of the spinal correction system are configured to allow and/or preserve motion of a patient. In one embodiment, the growth rod is configured for fixation between tissue of a first rib and tissue of a second rib. In one embodiment, the growth rod is configured for fixation between tissue of a rib and tissue of a spine. In one embodiment, the growth rod is configured for fixation between tissue of a rib and tissue of a pelvis.

In some embodiments, the spinal correction system includes a growth rod that is configured for attachment to tissue and/or a bony anatomy via, for example, hooks, screws and/or wires. In some embodiments, the spinal correction system includes a growth rod configured for passive lengthening, such as, for example, lengthening through daily activity. In some embodiments, the spinal correction system includes a growth rod configured for active lengthening by, for example, a surgical instrument, such as, for example, a driver that is inserted through a stab incision created with a patient and engageable with an actuator of the growth rod for lengthening the growth rod. In some embodiments, the growth rod may be actively lengthened while the patient is subject to a local anesthetic and/or monitored with medical imaging, such as, for example, fluoroscopy.

In one embodiment, the spinal correction system comprises a growth rod including a body, such as, for example, an engine, a telescoping rod and a fixed rod. In one embodiment, the spinal correction system comprises a growth rod including a curved body configured for disposal with ribs. In one embodiment, the growth rod includes a body having a 200 millimeter (mm) radius of curvature, a 4 mm thickness, and a 8 mm width. In some embodiments, the growth rod includes a body and rods having varying lengths and/or curvatures to accommodate different sized patients.

In some embodiments, the spinal correction system includes a growth rod configured for active lengthening via use of an actuator. In some embodiments, the spinal correction system includes a surgical instrument, such as, for example, a driver that periodically accesses the growth rod by making a stab incision in the patient to allow the driver to be inserted into a cam drive of the growth rod. In one embodiment, active lengthening includes rotation of the cam drive in either direction to lengthen the growth rod.

In some embodiments, this configuration provides for reduction of large incisions and lengthening instruments, and maintains tissue integrity for children patients thereby reducing complications and infections. In some embodiments, the growth rod is employed with a minimally invasive surgical procedure.

In some embodiments, the growth rod includes a curved, low profile body. In some embodiments, the growth rod includes rods at either end having a diameter of, for example, 4.75 mm. In one embodiment, the growth rod includes flat rods and/or small diameter rods. In some embodiments, the growth rod can have a body with various radius of curvature.

In some embodiments, the growth rod includes a case having a rod fixed therewith. A telescoping rod is connected to the case and translatable relative to the case and fixed rod. In some embodiments, the case includes one or more racks and one or more spring biased pawls for translating the telescoping rod. In some embodiments, the case includes a cam for translating the telescoping rod. In one embodiment, the growth rod includes a rotating cam configured to cause the rack to translate up and down relative to the case and fixed rod. In one embodiment, a first pawl is attached to the telescoping rod and engages the rack for upward translation of the telescoping rod. In one embodiment, as the rack translates downward, a second pawl engages the case and the telescoping rod remains stationary until the rack begins to translate upward again.

In some embodiments, one or all of the components of system 10 may be disposable, peel-pack, pre-packed sterile devices. One or all of the components of system 10 may be reusable. System 10 may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The present disclosure may also be alternatively employed with procedures for treating the lumbar, cervical, thoracic and pelvic regions of a spinal column. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, outer, inner, terminal (denoting position or location), left and right, posterior, anterior, and the like, are for illustrative purposes only and can be varied within the scope of the disclosure. For example, the references "superior" and "inferior" are relative and used only in the context to the other, and are not necessarily "upper" and "lower".

As used in the specification and including the appended claims, "treating" or "treatment" of a disease or condition refers to performing a procedure that may include administering one or more drugs to a patient in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (for example, preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, for example, arresting its development, or relieving the disease, for example, causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, muscle, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Referring to FIGS. 1-5, there are illustrated components of a surgical system including, for example, a spinal correction system 10.

The components of system 10 can be fabricated from biologically acceptable materials suitable for medical applications, including metals, synthetic polymers, ceramics and/or their composites. For example, the components of system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, composites of PEEK with resorbable polymers, or other resorbable polymers such as polyaetide, polyglycolide, polytyrosine carbonate, polycaroplaetohe and their combinations. Various components of system 10 may have material composites, including the above materials, to achieve various desired characteristics such as strength, rigidity, elasticity, compliance, biomechanical performance, durability and radiolucency or imaging preference. The components of system 10, individually or collectively, may also be fabricated from a heterogeneous material such as a combination of two or more of the above-described materials. The components of system 10 may be monolithically formed, integrally connected or include fastening elements and/or instruments, as described herein.

The components of spinal correction system 10 are employed, for example, with a mini-open, minimal access and/or minimally invasive including percutaneous surgical technique to attach an implant to tissue of a first bony anatomy and tissue of a second bony anatomy of a patient that has a spinal disorder. In one embodiment, the implant may be affixed to one or more selected sections of one or more bony anatomies of a patient, such as, for example, ribs, spine, pelvis and/or other anatomy while allowing for growth and adjustments to a concave side of a plurality of vertebrae for a correction treatment to treat various spine pathologies, such as, for example, adolescent idiopathic scoliosis and Scheuermann's kyphosis. In one embodiment, the implant is configured for fixation between tissue of a first rib and tissue of a second rib for treatment of a patient having a scoliotic disorder and suffering from congenital chest wall deformation. This configuration can include a growing rod, as described herein, connected with a rib cage to expand and support a deformed chest wall.

Figure 4:
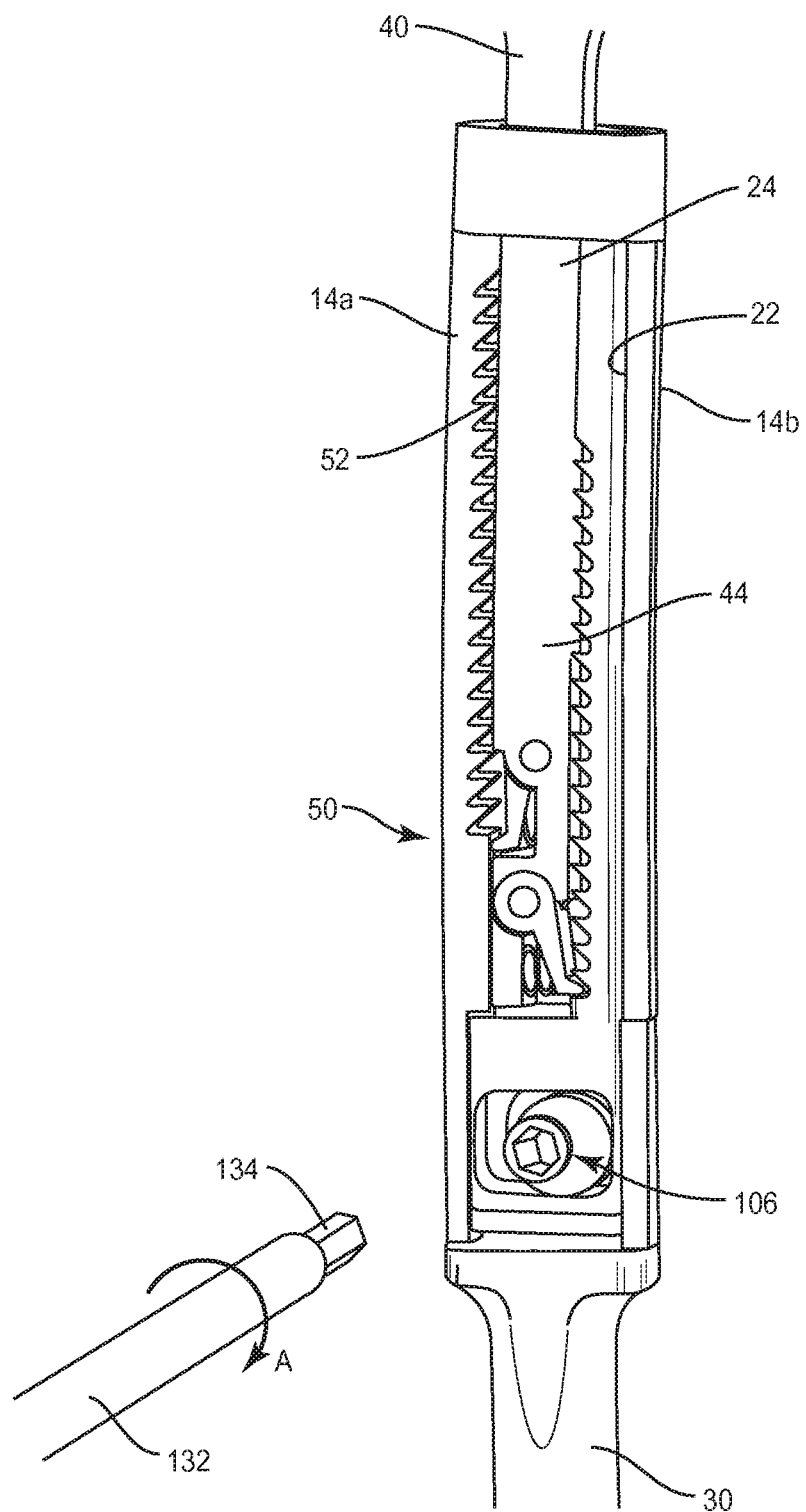
FIG. 4 is a perspective view of components, in part cutaway, of one embodiment of a spinal correction system in accordance with the principles of the present disclosure.

Spinal correction system 10 includes an implant, such as, for example, a growth rod 12. Growth rod 12 includes a body 13 that includes a case 14a, as shown in FIG. 4, which supports one or more components of system 10. Body 13 includes a cover, such as, for example, a sleeve 14b for enclosing and/or being connected with at least a portion of one or more components of system 10, as described herein. Body 13 extends between an end 16 and an end 18. Body 13 and sleeve 14b have an oblong cross section configuration. In some embodiments, body 13 and/or sleeve 14b may have an oval, triangular, square, polygonal, irregular, uniform, non-uniform, offset, staggered, undulating, arcuate, variable and/or tapered configuration and/or cross-section.

Figure 3:
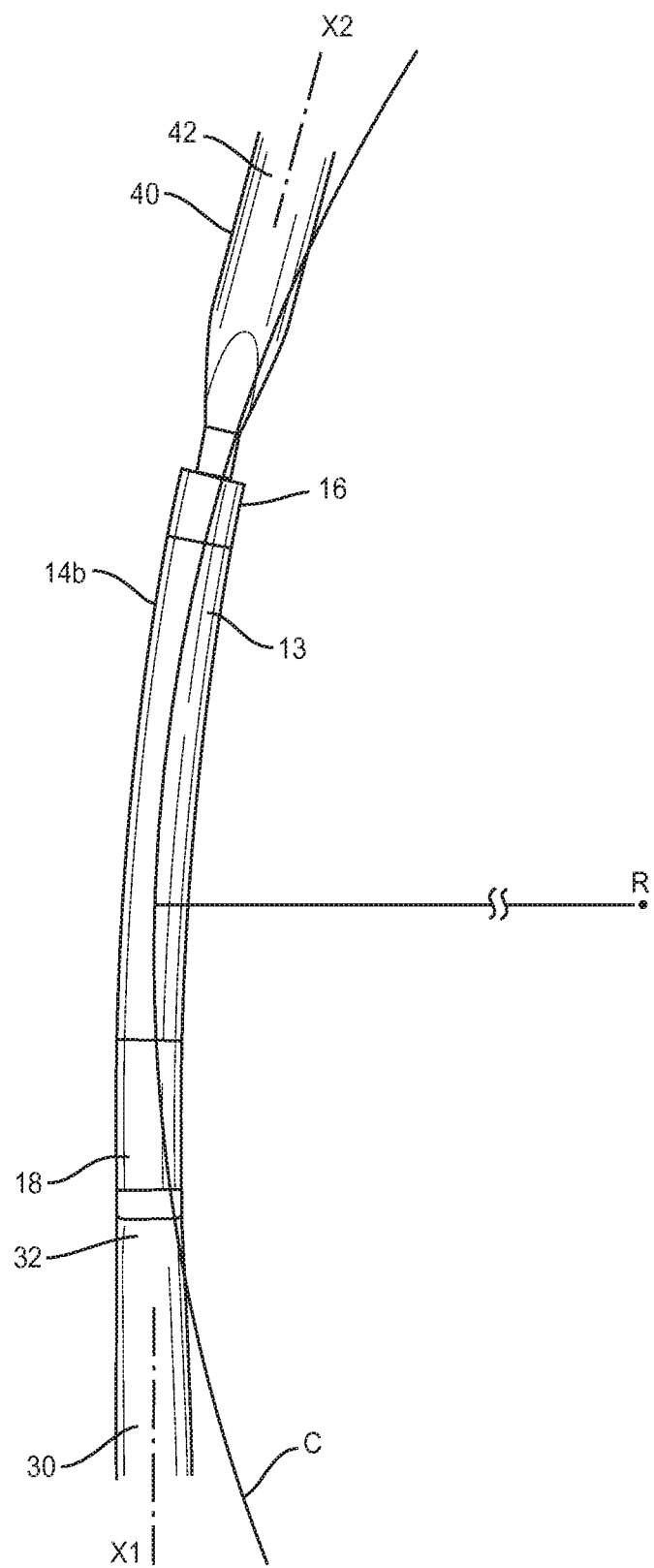
FIG. 3 is a side view of the components shown in FIG. 1.

Body 13 and sleeve 14b have an arcuate configuration, such as, for example, a curvature C corresponding to a radius of curvature R of body 13 measured from a medial thickness of body 13, as shown in FIG. 3. In some embodiments, body 13 includes a radius of curvature R measured from an outer surface 20 of sleeve 14b, which may include various portions and/or sides of body 13. In some embodiments, body 13 includes a radius of curvature R of 200 mm. In some embodiments, body 13 may include a range of curvatures and/or radii of curvature, such as, for example, a radius of curvature R of less than or greater than 200 mm.

Growth rod 12 includes a curved, low profile body 13. In some embodiments, growth rod 12 includes body 13 that is curved for disposal about ribs of a patient. In some embodiments, growth rod 12 includes body 13 having a curvature C, a 4 mm thickness of body 13, and an 8 mm width of body 13. In some embodiments, all or only a portion of outer surface 20 may have alternate surface configurations, such as, for example, rough, undulating, porous, semi-porous, dimpled and/or textured.

Sleeve 14b includes an inner surface 22 for enclosing one or more components of system 10. Surface 22 defines at least a portion of a cavity 24 for disposal of at least a portion of one or more components of system 10. Cavity 24 has a substantially oblong cross section. In some embodiments, cavity 24 may have alternate cross section configurations such as, for example, triangular, square, polygonal, irregular, uniform, non-uniform, offset, staggered, undulating, arcuate, variable and/or tapered. Surface 20 defines a portion of an opening 64 disposed adjacent end 18. Opening 64 is configured for alignment and disposal of one or more components of system 10, as described herein. In some embodiments, opening 64 is configured for disposal and/or mating engagement with a surgical instrument that is engageable with one or more components of system 10, as described herein.

A longitudinal element, such as, for example, a rod 30 is connected with case 14a. Rod 30 defines a longitudinal axis X1 and extends between an end 32 and an end 34. End 32 is fixed with and aligned for connection with end 18 such that rod 30 is fixed with body 13 along axis X1. End 32 includes a flange 33 having a planar face that abuts case 14a. In some embodiments, end 32 is monolithically formed with case 14a adjacent end 18. In some embodiments, end 32 is integrally connected or includes fastening elements connected with case 14a adjacent end 18.

End 34 connects with tissue to facilitate relative movement of the component parts of growth rod 12 in a configuration that allows for growth and adjustments to vertebrae for a correction treatment, as described herein. In some embodiments, end 34 may be affixed to one or more selected sections of one or more bony anatomies of a patient, such as, for example, ribs, spine, pelvis and/or other anatomy, as described herein.

A longitudinal element, such as, for example, a rod 40 is connected with case 14a. Rod 40 defines a longitudinal axis X2 and extends between an end 42 and an end 44. End 44 is attached with a ratchet 50, as described herein, of case 14a such that rod 40 is translatable along axis X2 and/or along curvature C and relative to body 13 and/or rod 30. End 42 is connected with tissue and is movable relative to rod 30 in a configuration that allows for growth and adjustments to vertebrae for a correction treatment, as described herein. In some embodiments, end 42 may be affixed to one or more selected sections of one or more bony anatomies of a patient, such as, for example, ribs, spine, pelvis and/or other anatomy, as described herein.

In some embodiments, rod 40 is attached with ratchet 50 such that rod 40 is incrementally translatable relative to rod 30 along axis X2 and/or curvature C. In some embodiments, rod 40 is attached with ratchet 50 such that rod 40 is incrementally translatable relative to rod 30 along axis X2 and/or curvature C via engagement of a surgical instrument with ratchet 50. In some embodiments, rod 40 is attached with ratchet 50 and connected with tissue such that spacing of tissue, for example, due to growth and/or adjustments to vertebrae, causes dynamic incremental movement of rod 40 relative to rod 30 along axis X2 and/or curvature C.

In some embodiments, rod 30 and/or rod 40 can be attached with tissue, as described herein, with a fastener. In some embodiments, system 10 can include one or more of fasteners that connect rod 30 and/or rod 40 with tissue in various orientations, such as, for example, series, parallel, offset, staggered and/or alternate vertebral levels. In some embodiments, one or more of fasteners may comprise multi-axial screws, sagittal angulation screws, pedicle screws, mono-axial screws, uni-planar screws, facet screws, fixed screws, tissue penetrating screws, conventional screws, expanding screws, wedges, anchors, buttons, dips, snaps, friction fittings, compressive fittings, expanding rivets, staples, nails, adhesives, posts, fixation plates and/or posts. In one embodiment, the fastener comprises a loop encircled about bony tissue.

Ends 34, 42 each have a substantially cylindrical cross section. In some embodiments, end 34 and/or end 42 can be variously configured, such as, for example, round, oval, oblong, square, triangular, rectangular, irregular, uniform, non-uniform, consistent and/or variable. Ends 34, 42 each have an outer surface and a uniform thickness/diameter. In some embodiments, the outer surface of ends 34, 42 may have various surface configurations, such as, for example, rough, threaded for connection with surgical instruments, arcuate, undulating, porous, semi-porous, dimpled, polished and/or textured. In some embodiments, the thickness defined by ends 34, 42 may be uniformly increasing or decreasing, or have alternate diameter dimensions along its length. In some embodiments, end 34 and/or end 42 has a diameter of 4.75 mm.

In some embodiments, the longitudinal element connected with body 13 can include a tether and/or tape. In some embodiments, the longitudinal element connected with body 13 can include a flexible configuration, which includes movement in a lateral or side to side direction and prevents expanding and/or extension in an axial direction upon fixation with tissue, as described herein. In some embodiments, all or only a portion of the longitudinal element may have a semi-rigid, rigid, flexible or elastic configuration, and/or have elastic and/or flexible properties such as the elastic and/or flexible properties corresponding to the material examples described above such that the longitudinal element provides a selective amount of expansion and/or extension in an axial direction. In some embodiments, the longitudinal element may be compressible in an axial direction. In some embodiments, the longitudinal element, for example, rod 30 and/or rod 40 can include a plurality of separately attachable or connectable portions or sections, such as bands or loops, or may be monolithically formed as a single continuous element. In some embodiments, the longitudinal element can include a transitioning structure from body 13 to tissue and may comprise a composite metal and/or plastic structure extending from body 13.

In some embodiments, the longitudinal element may have various lengths. In some embodiments, the longitudinal element may be braided, such as a rope, or include a plurality elongated elements to provide a predetermined force resistance. In some embodiments, the longitudinal element may be made from autograft and/or allograft, and be configured for resorbable or degradable applications. In some embodiments, the longitudinal element may include one or a plurality of flexible wires, staples, cables, ribbons, artificial and/or synthetic strands, rods, plates, springs, and combinations thereof. In one embodiment, the longitudinal element is a cadaver tendon. In one embodiment, the longitudinal element is a solid core. In one embodiment, the longitudinal element is tubular.

In one embodiment, body 13, rod 30 and/or rod 40 include sensors configured to measure and/or indicate displacement of components of growth rod 12, torque, force and/or pressure applied to growth rod 12 to facilitate management of therapy and treatment. For example, rod 30 and/or rod 40 can include a transducer in communication with a display module and processor connected, attached or embedded with body 13 to display displacement, torque, force and/or pressure. In some embodiments, growth rod 12 may include a sensor, such as, for example, one or more accelerometers, rotary capacitive sensors, a solid-state sensor incorporating an accelerometer or a potentiometer, solid-state sensors employing other physical properties (e.g., a magnetic field sensor or other device that employs magnetic resistance), angular position sensors, rotary position sensors, linear position sensors, mechanical or electromagnetic induction sensors, capacitive sensors and/or gate sensors.

Figure 5:
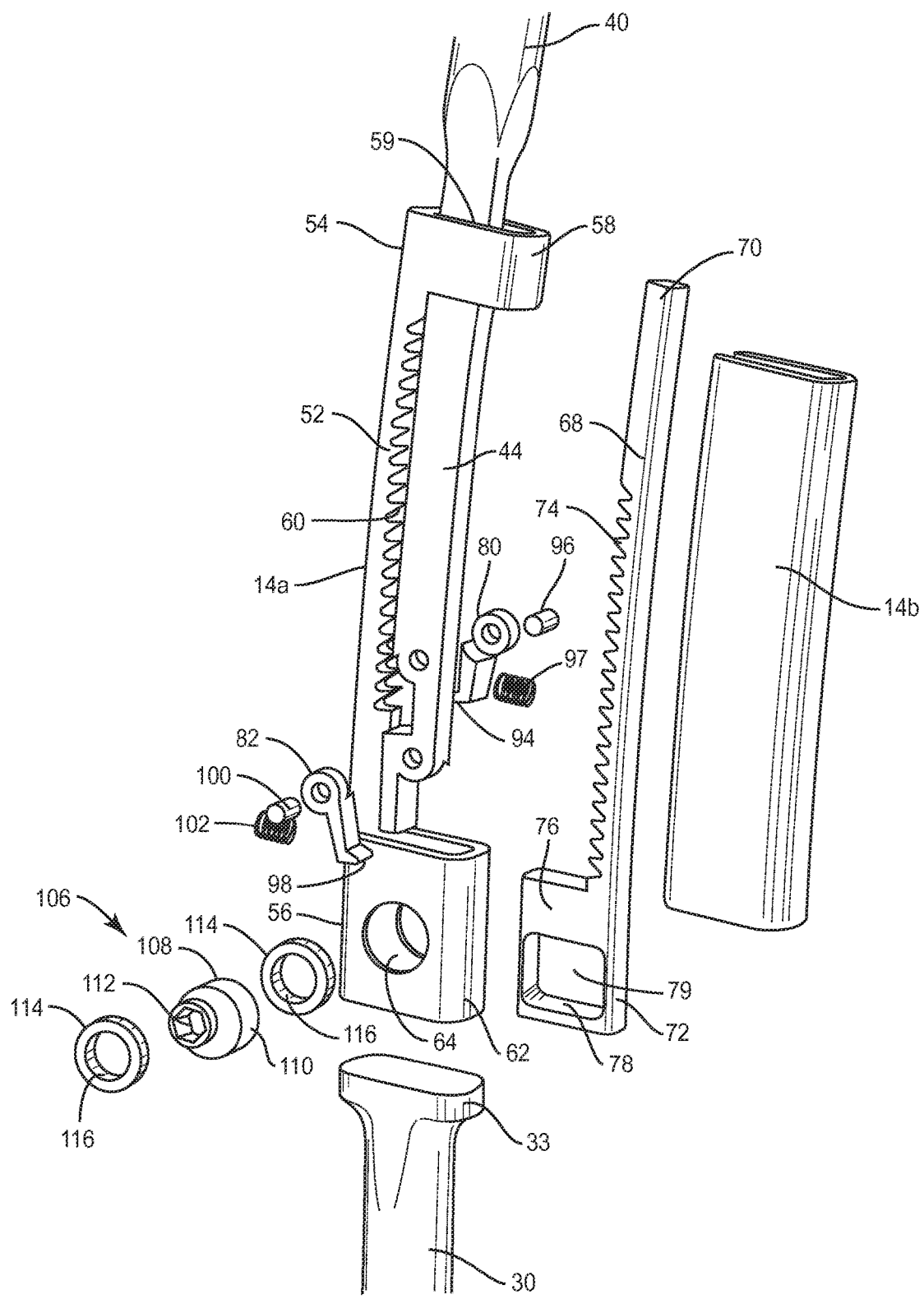
FIG. 5 is a perspective view of components, with parts separated, of one embodiment of a spinal correction system in accordance with the principles of the present disclosure.

Ratchet 50 is connected to end 44 and disposed in cavity 24 such that rod 40 is incrementally translatable relative to rod 30 along axis X2 and/or curvature C, as shown in FIGS. 4 and 5. Ratchet 50 includes a rack 52 defined with case 14a. Rack 52 extends between an end 54 and an end 56 of case 14a. End 54 includes a transverse support 58 that has an opening 59 configured for support and slidable relative movement of rod 40. Support 58 is disposed adjacent end 16. Rack 52 includes gear teeth 60 disposed in a linear configuration between ends 54, 56. End 56 includes a transverse support 62 that defines a portion of opening 64 and is configured for support and relative rotational movement of an actuator 106, as described herein.

Ratchet 50 includes a carriage comprising a rack 68, which extends between an end 70 and an end 72 of the carriage. End 70 is configured for moveable disposal in opening 59 such that rack 68 translates, in a direction as shown by arrow C in FIG. 6B, and in a direction as shown by arrow D in FIG. 6C, opposite to the direction shown by arrow C. Rack 68 includes gear teeth 74 disposed in a linear configuration between ends 70, 72.

End 72 includes a transverse support 76 having an inner surface 78. Surface 78 defines a transverse channel 79. Channel 79 has a non-circular configuration, such as, for example, substantially rectangular for movable disposal of actuator 106. Channel 79 may have various configurations, such as, for example, oval, oblong, triangular, elliptical, square, polygonal, irregular, uniform, non-uniform, variable and/or tapered. Channel 79 is configured for alignment with opening 64 and support and relative rotational movement of actuator 106.

Ratchet 50 includes pawls 80, 82. Pawl 80 includes a gear tooth 94. Gear tooth 94 is configured for engagement with gear teeth 60 of rack 52. A pin 96 connects pawl 80 with rod 40. Pawl 80 is biased into engagement with rack 52 with a biasing member, such as, for example a spring 97. Pawl 82 includes a gear tooth 98. Gear tooth 98 is configured for engagement with gear teeth 74 of rack 68. Pin 100 connects pawl 82 with rod 40. Pawl 82 is biased into engagement with rack 68 with a biasing member, such as, for example, a spring 102.

Pawls 80, 82 are rotatable relative to rod 40 such that pawls 80, 82 pivot about pins 96, 100 respectively. Pawl 80 pivots about pin 96 to facilitate releasable engagement of tooth 94 with teeth 60 and pawl 82 pivots about pin 100 to facilitate releasable engagement of tooth 98 with teeth 74 to translate rod 40 incrementally relative to rod 30 along axis X2 and/or curvature C, as described herein.

Actuator 106 includes a cam 108 having an outer surface 110 and a cylindrical configuration. Cam 108 is rotatable within opening 64 and channel 79 such that outer surface 110 engages surface 78 to cause axial translation of rod 40. Cam 108 includes a socket 112 having a hexagonal configuration. Socket 112 is configured for engagement with an instrument, as described herein. Socket 112 is offset from a central transverse axis of cam 108 such that cam 108 is rotatable to follow an off center transverse axis path relative to the central transverse axis. Actuator 106 includes washers 114 each including an inner surface 116. Washers 114 are disposed with cam 108, which are mounted with opening 64.

Actuator 106 is disposed with case 14*a* and is connected to ratchet 50 to facilitate incremental movement of rod 40 relative to rod 30 in at least one axial direction. Actuator 106 is rotatable in a direction, such as, for example, a clockwise direction and a direction, such as, for example, a counter clockwise direction to facilitate movement of rod 40 in at least one axial direction.

In operation, as shown in FIGS. 6A-6E, spinal correction system 10 includes an instrument, such as, for example, a drive tool 132, as shown in FIG. 4. Drive tool 132 is manipulated to engage cam 108 for rotation thereof to facilitate incremental movement of rod 40 relative to rod 30. Drive tool 132 includes a tip 134 having a hexagonal cross section configuration for mating with socket 112. In some embodiments, tip 134 may have alternative configurations, such as, for example, those alternatives described herein.

Tip 134 is inserted into opening 64 and passes through inner surface 116. Cam 108 is disposed in a first orientation. End 72 is disposed adjacent an end most surface of case 14*a* and pawls 80, 82 are disposed to engage racks 74, 60, respectively, in a gear mesh fixation. Tip 134 is caused to engage socket 112 and drive tool 132 is rotated in a clockwise direction, as shown by arrow A in FIG. 4. Drive tool 132 rotates cam 108 such that the circular configuration of outer surface 110 engages the non-circular configuration of surface 78 along an off center path of rotation.

Figure 6A:
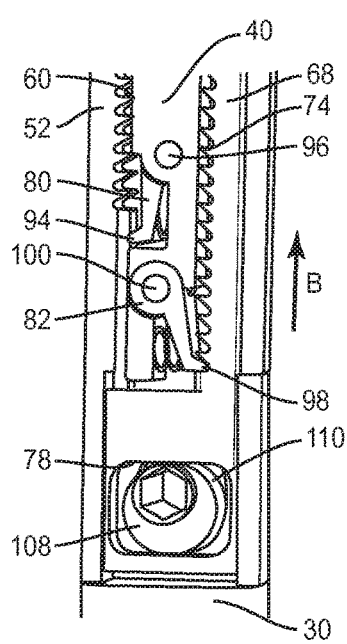
FIGS. 6A-6E are cutaway views of the components shown in FIG. 1.
Figure 6B:
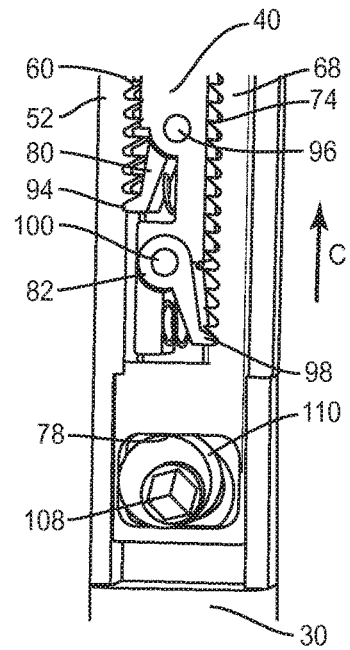

Engagement of outer surface 110 with surface 78 translates rack 68, in the direction shown by arrow B in FIG. 6A, such that tooth 94 advances along rack 52 and/or teeth 60 causing rod 40 to translate relative to rod 30 in the axial direction shown by arrow C in FIG. 6B. Pawls 80, 82 are biased outwardly such that the gear teeth are disposed in a releasable fixation and a fixed position with racks 52, 68.

Figure 6C:
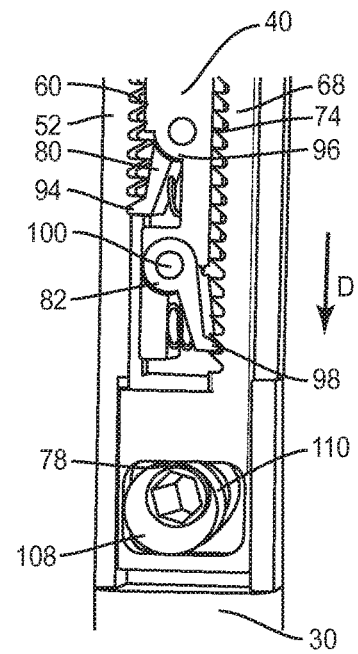
Figure 6D:
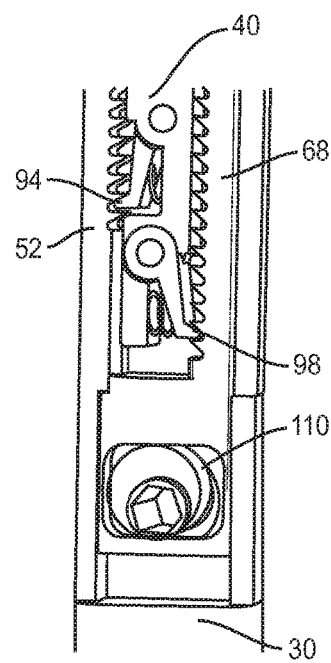
Figure 6E:
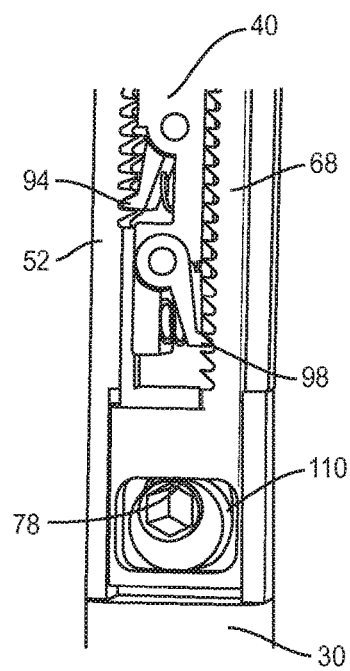

Further rotation of cam 108 within channel 79 causes rack 68 to translate in the direction shown by arrow D in FIG. 6C, such that tooth 98 advances along teeth 74 and/or rack 68. As drive tool 132 is further rotated, cam 108 translates rack 68 in the direction shown by arrow B in FIG. 6A, such that tooth 94 advances along teeth 60 causing rod 40 to translate relative to rod 30 in the axial direction shown by arrow C in FIG. 6B. This configuration facilitates incremental movement of rod 40 relative to rod 30 and/or body 13, in the direction shown by arrow C. Movement of rod 40 relative to rod 30 expands the overall length of growth rod 12 to be used, for example, with a procedure for stabilization of vertebrae, initial implantation and/or to compensate for patient growth. In one embodiment, cam 108 may be rotated in a clockwise direction and a counter-clockwise direction to advance rod 40 in one or more axial directions. In one embodiment, rod 40 is advanced relative to rod 30 in one axial direction only. In one embodiment, movement of rod 40 relative to rod 30 and/or body 13 expands the overall length of growth rod 12 to compensate for axial rotation of a body.

In some embodiments, spinal correction system 10 is configured for non-invasive lengthening to compensate for patient growth. For example, during patient growth, a force, such as, for example, an expansion force, due to separation of anatomical body portions attached to growth rod 12, is applied to rod 40 that causes dynamic incremental movement of rod 40, independent of actuator 106, relative to rod 30. In one embodiment, dynamic incremental movement of rod 40 is responsive to, caused by and/or associated with motion of a spine and adjacent anatomical portions of a body of a patient. In one embodiment, such motion includes motion of the spine and adjacent anatomical portions due to the natural load bearing and dynamic characteristics of the spine, which may include flexion, extension, rotation and lateral bending. In one embodiment, such motion includes motion of the spine and adjacent anatomical portions due to external loads, which may include axial, shear, linear, non-linear, angular, torsional, compressive and/or tensile loads, applied to the body of the patient.

Upon application of the expansion force to end 42, rack 68 is drawn, in the axial direction shown by arrow B in FIG. 6A, towards end 16 such that tooth 98 advances along teeth 74 and tooth 94 advances along teeth 60, as described herein. Pawls 80, 82 are biased outwardly such that the gear teeth are disposed in a releasable mesh fixation and a fixed position with racks 52, 68. In one embodiment, the forces are applied to rod 30.

As rack 68 is drawn and advanced, pawls 80, 82 become releasably fixed in an advanced position with racks 52, 68 such that the respective rack and pawl teeth are disposed in a releasable mesh fixation. Rod 40 is advanced, in the direction shown by arrow B in FIG. 6A, via advancement of pawls 80, 82 with racks 52, 68 as described, and rod 40 is advanced, in the direction shown by arrow B, according to the expansion force, such as, for example, an amount of growth between the anatomical portions connected to growth rod 12. The mesh engagement of the gear teeth of pawls 80, 82 with racks 52, 68 prevents contraction and/or axial movement of rod 40 relative to rod 30, in a direction opposite to the axial direction shown by arrow B, and permits further expansion and/or advancement of rod 40 relative to rod 30, in the axial direction shown by arrow B, according to other forces applied to growth rod 12 and/or subsequent patient growth. This configuration provides dynamic incremental movement of rod 40 relative to rod 30, in the direction shown by arrow B, to be used, for example, for stabilization of vertebrae and non-invasive lengthening and/or compensation for patient growth.

In assembly, operation and use, a system including spinal correction system 10, similar to the systems and methods described herein, is employed with a surgical procedure, such as, for example, a correction treatment to treat adolescent idiopathic scoliosis and/or Scheuermann's kyphosis of a spine. In some embodiments, one or all of the components of spinal correction system 10 can be delivered or implanted as a pre-assembled device or can be assembled in situ. The components of spinal correction system 10 may be completely or partially revised, removed or replaced.

Figure 7:
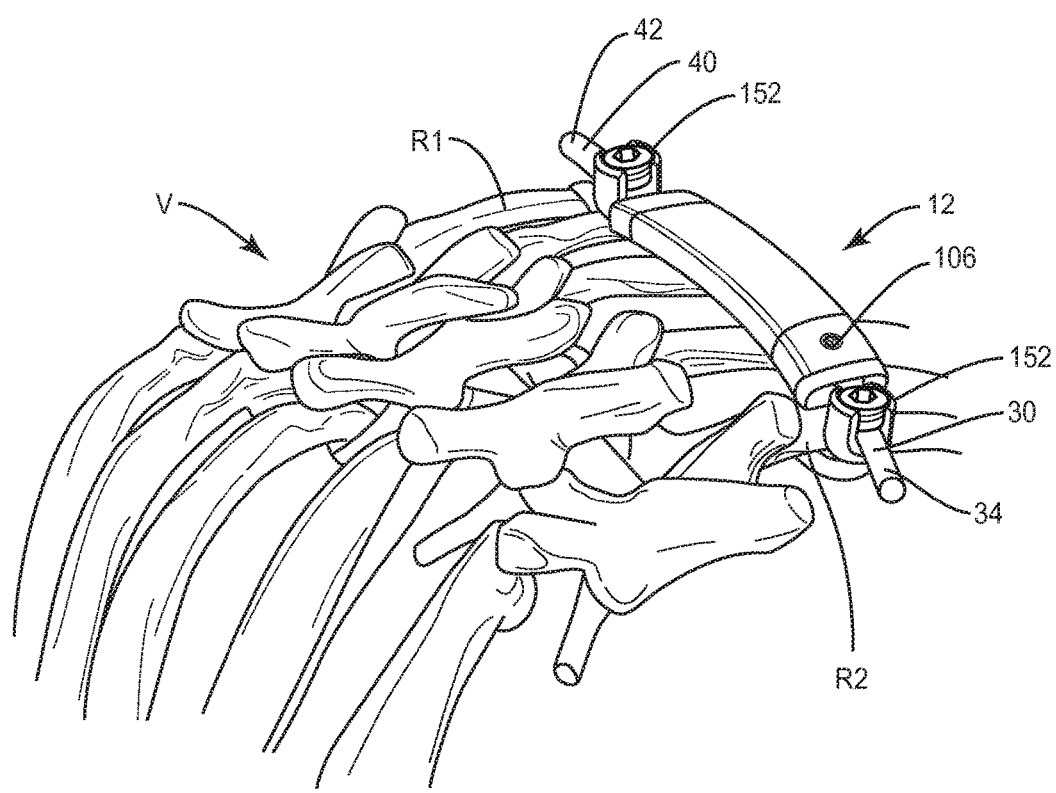
FIG. 7 is a perspective view of components of one embodiment of a spinal correction system in accordance with the principles of the present disclosure disposed with a bony anatomy.

For example, spinal correction system 10 can be employed with a surgical correction treatment of an applicable condition or injury of an affected section of a spinal column and adjacent areas within a body. In some embodiments, as shown in FIG. 7, growth rod 12 is configured for fixation between tissue, such as, for example, a rib R1 and tissue, such as, for example, a rib R2 for treatment of a patient having a scoliotic disorder of vertebrae V and suffering from congenital chest wall deformation. Growth rod 12 is connected with ribs R1, R2 of a rib cage to expand and support a deformed chest wall.

In use, to treat a selected section of vertebrae V and adjacent areas within a body, a medical practitioner obtains access to a surgical site including ribs R1, R2 adjacent vertebrae V in any appropriate manner, such as through incision and retraction of tissues. In some embodiments, spinal correction system 10 can be used in any existing surgical method or technique including open surgery, mini-open surgery, minimally invasive surgery and percutaneous surgical implantation, whereby ribs R1, R2 are accessed through a mini-incision, or sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for implantation of components of system 10 including growth rod 12. A preparation instrument (not shown) can be employed to prepare tissue surfaces of ribs R1, R2, as well as for aspiration and irrigation of a surgical region.

A fastener, such as, for example, a hook assembly 152 is connected with end 34 of rod 30 to attach rod 30 with rib R2. A hook assembly 152 is connected with end 42 of rod 40 to attach with rib R1. Hook assemblies 152 attach growth rod 12 with ribs R1, R2 for treating a scoliotic disorder and/or congenital chest wall deformation to expand and support a deformed chest wall of a rib cage.

Upon attachment of growth rod 12 with ribs R1, R2, a surgical instrument, similar to tool 132 described herein, is manipulated to engage actuator 106 to facilitate incremental movement of rod 40 such that rod 40 is incrementally translatable relative to rod 30 along axis X2 and/or curvature C, similar to the examples and embodiments described herein. In some embodiments, growth rod 12 provides dynamic incremental movement of rod 40 relative to rod 30, similar to that described herein.

One or more of the components of spinal correction system 10 can be made of radiolucent materials such as polymers. Radiomarkers may be included for identification under x-ray, fluoroscopy, CT or other imaging techniques. In some embodiments, the use of surgical navigation, micro-surgical and image guided technologies may be employed to access, view and repair spinal deterioration or damage, with the aid of spinal correction system 10. In one embodiment, spinal correction system 10 may include one or a plurality of growth rods 12 for use with one or more bony anatomies of a patient, as described herein.

In one embodiment, spinal correction system 10 includes an agent, which may be disposed, packed, coated or layered within, on or about the components and/or surfaces of spinal correction system 10. In some embodiments, the agent may include bone growth promoting material, such as, for example, bone graft to enhance fixation of the components and/or surfaces of spinal correction system 10 with vertebrae. In some embodiments, the agent may include one or a plurality of therapeutic agents and/or pharmacological agents for release, including sustained release, to treat, for example, pain, inflammation and degeneration. Upon completion of the procedure, the non-implant components, instruments and assemblies are removed and the incision(s) is closed.

In some embodiments, the components of spinal correction system 10 may be employed to treat progressive idiopathic scoliosis with or without sagittal deformity in either infantile or juvenile patients, including but not limited to prepubescent children, adolescents from 10-12 years old with continued growth potential, and/or older children whose growth spurt is late or who otherwise retain growth potential. In some embodiments, the components of spinal correction system 10 and/or the methods of use described herein may be used to prevent or minimize curve progression in individuals of various ages.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:
1. A spinal correction implant comprising:
 a body extending between a first end and a second end, the body having a curvature;
 a first longitudinal element connected with the first end;
 a ratchet disposed with the body; and
 a second longitudinal element connected to the ratchet and being incrementally movable relative to the body, the ratchet comprising a first rack and a first pawl engageable with the first rack, the first pawl being pivotable about a first pin that extends through the second longitudinal element, the ratchet further comprising a second rack and a second pawl engageable with the second rack, the second pawl being pivotable about a second pin that extends through the second longitudinal element.

2. A spinal correction implant as recited in claim 1, wherein the first longitudinal element is configured to be connected with a first tissue and the second longitudinal element is configured to be connected with a second tissue such that spacing of the tissue causes dynamic incremental movement of the second longitudinal element relative to the body.

3. A spinal correction implant as recited in claim 1, further comprising an actuator connected with the ratchet, the actuator being engageable to cause incremental movement of the second longitudinal element relative to the body.

4. A spinal correction implant as recited in claim 1, wherein at least one of the longitudinal elements includes a fastener configured to be connected with rib tissue.

5. A spinal correction implant as recited in claim 1, wherein the body comprises an oblong cross section configuration.

6. A spinal correction implant as recited in claim 1, wherein the first longitudinal element is fixed relative to the body.

7. A spinal correction implant as recited in claim 1, wherein the ratchet comprises a support connected with the second longitudinal element, the support comprising an opening having the second longitudinal element slidably positioned therein.

8. A spinal correction implant as recited in claim 1, wherein the first pawl is biased into engagement with the first rack.

9. A spinal correction implant as recited in claim 1, wherein the second pin is spaced apart from the first pin.

10. A spinal correction implant as recited in claim 1, wherein the pawls are biased into engagement with the respective rack.

11. A spinal correction implant as recited in claim 1, wherein the second longitudinal element is disposed in a telescopic configuration with the body.

12. A spinal correction implant as recited in claim 1, further comprising an actuator connected with the ratchet, the actuator being rotatable to facilitate movement of the second longitudinal element.

13. A spinal correction implant as recited in claim 12, wherein the actuator includes a rotatable cam engageable with the ratchet.

14. A spinal correction implant as recited in claim 1, wherein the second longitudinal element is connected with the ratchet and configured for movement in a first axial direction only.

15. A spinal correction implant as recited in claim 1, wherein the body has a radius of curvature measured from a medial thickness of the body, the radius of curvature being greater than 0 mm.

16. A spinal correction implant as recited in claim 1, wherein the pawl directly engages the rack.

17. A spinal correction implant comprising:
- a body extending between a first end and a second end, the body having a curvature;
- a ratchet disposed with the body and comprising a first rack and a second rack, the ratchet further comprising a first pawl engageable with the first rack and a second pawl engageable with the second rack;
- a fixed rod connected with the first end;
- a telescopic rod connected with the ratchet and being incrementally movable relative to the body, the pawls each being pivotable about a pin that extends through the telescopic rod, the pins being spaced apart from one another along a length of the telescopic rod; and
- an actuator that is engageable to cause incremental movement of the second longitudinal element relative to the body.

18. A spinal correction implant as recited in claim 17, wherein the actuator is rotatable to facilitate movement of the second longitudinal element.

19. A spinal correction implant as recited in claim 17, wherein the actuator includes a rotatable cam engageable with the ratchet.

20. A spinal correction implant comprising:
- a body extending between a first end and a second end;
- a first longitudinal element connected with the first end;
- a ratchet disposed with the body; and
- a second longitudinal element connected to the ratchet and being incrementally movable relative to the body,
- wherein the ratchet comprises a first rack and a second rack connected with the second longitudinal element, the ratchet further comprising a first pawl engageable with the first rack and a second pawl engageable with the second rack to facilitate movement of the second longitudinal element, the first pawl being pivotable about a first pin and the second pawl being pivotable about a second pin, at least one of the pins extending through the second longitudinal element.

\* \* \* \* \*

UNITED STATES PATENT AND TRADEMARK OFFICE
CERTIFICATE OF CORRECTION

PATENT NO. : 9,833,262 B2  
APPLICATION NO. : 14/450831  
DATED : December 5, 2017  
INVENTOR(S) : Lim et al.

Page 1 of 1

It is certified that error appears in the above-identified patent and that said Letters Patent is hereby corrected as shown below:

In the Specification

In Column 2, Line 24, delete "fiat" and insert -- flat --, therefor.

In Column 3, Line 67, delete "dearly" and insert -- clearly --, therefor.

In Column 7, Line 7, delete "dips," and insert -- clips, --, therefor.

Signed and Sealed this  
Eighth Day of May, 2018

Andrei Iancu  
*Director of the United States Patent and Trademark Office*